(12) United States Patent
Aegerter et al.

(10) Patent No.: US 10,048,181 B2
(45) Date of Patent: Aug. 14, 2018

(54) DEVICE FOR PERFORMING A BENDING TEST

(71) Applicants: Johannes Aegerter, Hennef (DE); Stefan Keller, Bonn (DE)

(72) Inventors: Johannes Aegerter, Hennef (DE); Stefan Keller, Bonn (DE)

(73) Assignee: Hydro Aluminium Rolled Products GmbH, Grevenbroich (DE)

( * ) Notice: Subject to any disclaimer, the term of this patent is extended or adjusted under 35 U.S.C. 154(b) by 0 days.

(21) Appl. No.: 15/467,859

(22) Filed: Mar. 23, 2017

(65) Prior Publication Data

US 2017/0191916 A1     Jul. 6, 2017

Related U.S. Application Data

(63) Continuation of application No. PCT/EP2015/071586, filed on Sep. 21, 2015.

(30) Foreign Application Priority Data

Dec. 23, 2014  (DE) .......................... 10 2014 119 485

(51) Int. Cl.
| | |
|---|---|
| *G01N 3/20* | (2006.01) |
| *G01N 3/04* | (2006.01) |
| *G01N 3/08* | (2006.01) |

(52) U.S. Cl.
CPC ................ *G01N 3/20* (2013.01); *G01N 3/04* (2013.01); *G01N 3/08* (2013.01);
(Continued)

(58) Field of Classification Search
CPC .. G01N 3/20; G01N 3/04; G01N 3/08; G01N 2203/0023; G01N 2203/0252;
(Continued)

(56) References Cited

U.S. PATENT DOCUMENTS

| 1,872,047 A | * | 8/1932 | Templin | ................... | G01N 3/04 |
| | | | | | 24/136 R |
| 2,350,577 A | * | 6/1944 | Vordahl | ................... | G01N 3/04 |
| | | | | | 73/833 |

(Continued)

FOREIGN PATENT DOCUMENTS

| CN | 103969118 A | 8/2014 |
| DE | 31 01 422 A1 | 8/1982 |

(Continued)

*Primary Examiner* — Lisa Caputo
*Assistant Examiner* — Philip Cotey
(74) *Attorney, Agent, or Firm* — Reinhart Boerner Van Deuren P.C.

(57) ABSTRACT

Embodiments relate to a device for performing a bending test having a base plate, counter bearings connected via the base plate, bearing blocks which in each case comprise a support for applying a bending sample, and a bending punch or a bending rail for exerting a force on a bending sample. The distance of the supports can be set precisely and in a force resistant manner by abutting the counter bearings and the bearing blocks against each other via contact surfaces inclined to the base plate. Further provided is a method for performing a bending test using a device according to the invention, in the case of which a bending sample is applied on the supports and in the case of which a force is exerted between the supports on the bending sample.

18 Claims, 9 Drawing Sheets

(52) U.S. Cl.
CPC ............ *G01N 2203/0023* (2013.01); *G01N 2203/0252* (2013.01); *G01N 2203/0264* (2013.01); *G01N 2203/0278* (2013.01); *G01N 2203/04* (2013.01)

(58) Field of Classification Search
CPC ... G01N 2203/0264; G01N 2203/0278; G01N 2203/04
See application file for complete search history.

(56) References Cited

U.S. PATENT DOCUMENTS

| | | | | |
|---|---|---|---|---|
| 3,142,174 | A * | 7/1964 | Baker | G01N 3/20 269/8 |
| 3,403,549 | A * | 10/1968 | Griffin | G01N 3/04 73/859 |
| 4,213,349 | A * | 7/1980 | Miura | G01N 3/20 73/847 |
| 4,537,080 | A * | 8/1985 | Christiansen | G01N 3/04 73/854 |
| 4,573,360 | A * | 3/1986 | Yoneda | G01N 3/20 73/850 |
| 4,625,563 | A * | 12/1986 | Dawson | G01N 3/20 73/850 |
| 4,656,872 | A * | 4/1987 | Fischer | G01N 3/20 73/850 |
| 4,677,856 | A * | 7/1987 | Fischer | G01N 3/00 73/850 |
| 4,730,498 | A * | 3/1988 | Blanch | G01N 3/20 73/852 |
| 4,941,359 | A | 7/1990 | Quinn et al. | |
| 5,277,069 | A * | 1/1994 | Cussac | G01N 3/18 73/853 |
| 5,606,134 | A * | 2/1997 | Stieber | G01N 3/20 73/849 |
| 6,216,531 | B1 * | 4/2001 | Zhou | G01N 3/04 73/150 A |
| 6,234,029 | B1 * | 5/2001 | Liang | B23K 31/12 73/850 |
| 8,448,522 | B2 * | 5/2013 | Martin | G01N 3/04 73/856 |
| 2002/0166387 | A1 * | 11/2002 | Grote | G01B 11/16 73/800 |
| 2005/0241405 | A1 * | 11/2005 | Calloch | G01N 3/20 73/812 |
| 2009/0139344 | A1 * | 6/2009 | Lindeman | G01N 3/04 73/859 |
| 2011/0056304 | A1 * | 3/2011 | Hsueh | G01N 3/24 73/826 |
| 2012/0192638 | A1 * | 8/2012 | Zelinsky | G01N 3/08 73/150 A |
| 2014/0174193 | A1 * | 6/2014 | Kim | G01N 1/286 73/821 |

FOREIGN PATENT DOCUMENTS

| | | |
|---|---|---|
| FR | 2 735 235 A1 | 12/1996 |
| JP | 125311 | 6/1940 |
| JP | 54-184191 U1 | 2/1977 |
| JP | 53-113682 U1 | 6/1978 |
| JP | 60-168037 A | 8/1985 |
| JP | 2005-180972 A | 7/2005 |
| JP | 2006-78358 A | 3/2006 |
| JP | 2009/008665 A | 1/2009 |

* cited by examiner

DEVICE FOR PERFORMING A BENDING TEST

CROSS-REFERENCE TO RELATED PATENT APPLICATIONS

This patent application is a continuation of PCT/EP2015/071586, filed Sep. 21, 2015, which claims priority to German Application No. 10 2014 119 485.3, filed Dec. 23, 2014, the entire teachings and disclosure of which are incorporated herein by reference thereto.

FIELD OF INVENTION

The invention relates to a device for performing a bending test having a base plate, having counter bearings connected via the base plate, having bearing blocks, which in each case comprise a support for applying a bending sample and having a bending punch or bending rail for exerting a force on a bending sample. Furthermore, the invention relates to a method for performing a bending test using a device according to the invention.

BACKGROUND OF INVENTION

Bending tests are known from the prior art as standard methods for characterising mechanical material properties. In the case of bending tests, a bending sample is usually arranged and optionally clamped on a mount. Subsequently, the bending sample is subjected to a mechanical load, for example to a continuously increasing force along a determined direction or to a force alternating in direction. By measuring a deformation caused by the force, in particular a bending angle or also a break angle, mechanical characteristic values of the material of the sample can be directly measured or calculated.

Useful variants of the bending test are the so-called 3 point bending test, in particular as a platelet bending test or the 4 point bending test. The bending sample is applied on two supports (the first two points). Using a bending punch or bending rail, a force is exerted between the supports on the bending sample, either using a bending punch or bending rail with a contact point (in the 3 point bending test) or using a bending punch or bending rail with two contact points (in the 4 point bending test). The sample between the supports is deformed by the force exerted by the bending punch or bending rail, for example in the 3 point bending test substantially in a V-shape with a determined opening angle or bending angle. For example, a characteristic curve is thereby recorded, in the case of which the force over the punch movement is measured and evaluated.

In such bending tests, the measurement result is dependent on the distance of the supports. What is problematic in this case is that the forces exerted on the supports increase very strongly with increasing bending angle such that the distance of the supports during a bending test can change with the bending angle through the yielding of the measuring device and thus the measurement values are distorted. The distance of the counter bearings should be kept constant as far as possible even under high forces in order to obtain more precise measurement results.

At the same time, it is, however, often desirable for the distance of the supports to be adjustable. In this case, different distances of the supports are in particular used for different sample geometries and/or bending punch geometries. Different distances can also be used within a series of measurements for a sample geometry.

DE 31 01 422 A1 describes a device for performing a bending rest having supports located on bearing blocks, wherein the bearing blocks are arranged adjustably on a base plate. The bearing blocks are thereby clasped in a groove on the base plate and displaceable towards each other via a thread shaft. The distance of the supports can thus be set by positioning the bearing blocks.

What is disadvantageous here however, is, on the one hand that the fixation of the bearing blocks against each other via the thread shaft may initially be subject to a certain play, which a thread connection involves. On the other hand, in the case of a bending test the thread shaft is also loaded via a bending force with height of the bearing blocks as a lever, which, in the case of larger forces results in a change of the distance of the supports. Hitherto, a compromise between precise adjustability of the distance of the supports and a high force resistance of the distance of the supports or a high rigidity of the measuring device had to be made.

BRIEF SUMMARY OF THE INVENTION

Proceeding from the prior art, the technical problem underlying the present invention is to specify a device and a method for performing a bending test, by means of which the disadvantages from the prior art can be avoided and in particular the distance of the supports can be adjusted precisely and in a force resistant manner.

According to a first technical teaching of the present invention, this technical problem concerning a device is solved by the counter bearings and the bending blocks abutting against each other via contact surfaces inclined towards the base plate.

The device according to the invention comprises counter bearings which are connected via a base plate and which can receive the forces resulting from the bending test on the device. In this case, the dimensions and the material of the counter bearings and the base plate may be designed corresponding to the loads in the bending test. The unit of the base plate with the counter bearings is designed rigidly and in particular in a non-adjustable manner.

The supports for supporting a bending sample are arranged on bearing blocks. The bearing blocks serve to transfer the bending forces from the supports to the counter bearings in the case of a bending test. The bearing blocks are, to this end, inserted into the device between the counter bearings.

According to the invention, the counter bearings and the bearing blocks abut against each other via contact surfaces inclined towards the base plate. The transfer of force from the bearing blocks to the counter bearings can be effected via these contact surfaces. As a result of the fact that the contact surfaces are designed in an inclined manner, the forces acting on the bending device during the bending test are absorbed in an improved manner. In particular, the inclination of the contact surfaces is designed such that during the bending test, the majority of the transferred forces constantly acts perpendicular to the contact surfaces. In this case, the inclined contact surfaces of the counter bearings can form an angle of less than 90°, in particular between 70° and 90°, preferably between 75° and 85° to the base plate, wherein the angle from the base plate to the contact surface within the counter bearing is measured. The contact surfaces of the counter bearings to each other can in this case form an open angle, approximately in a V-shape with the base plate as the base surface.

It is conceivable to set a change of the distance of the bearing blocks and thus the distance of the supports by using differently dimensioned bearing blocks. In a preferred embodiment of the device according to the invention, means for the change of position of the bearing blocks perpendicular and/or parallel to the base plate are, however, provided. Due to the inclined contact surfaces of counter bearings and bearing blocks, a change of the distance of the supports can be effected with a change of position of the bearing blocks parallel and/or perpendicular to the base plate. If the position of the bearing blocks is changed perpendicular to the base plate, then a change of the position of the bearing blocks parallel to the base plate and thus a change of the distance of the supports is also indirectly effected via the inclined contact surfaces. Advantageously, the device continues to have the same stability and rigidity when the distance of the supports has been changed, since the forces can be transferred in the same manner via the contact surfaces between bearing blocks and counter bearings. A change of the position of the bearing blocks parallel to the base plate effects a direct change of the distance of the supports. A change of position of the supports only parallel to the base plate can also be achieved by using the inclined contact surfaces according to one embodiment. The advantage is that the height of the sample is not changed relative to the bending punch in this case.

By selecting the angle of the inclined contact surfaces close to 90°, a very fine adjustment of the distance of the counter bearings can also be enabled without less stable mechanics in the form of a fine thread or the like having to be used. The angle of the inclined contact surfaces predefines, in this case, the transmission ratio of the change of position perpendicular to the base plate to the change of position parallel to the base plate via a tangent function. An angle of contact surface to base plate of between 70° and 90°, in particular between 75° and 85° is preferred here. An angle of 80.54° for example results in a transmission of approximately 4:1 between the positioning of the bearing blocks perpendicular and parallel to the base plate. The base plate and the counter bearings, in particular the angle of contact surface to base plate are preferably formed symmetrically, i.e. the arrangement of base plate and counter bearings has a mirror-symmetrical plane and the angle of the contact surfaces of the counter bearings are alternately equal. This type of design causes the bending punch or the bending rail to be aligned further centrally to the supports after a single alignment of the device and central positioning of bending punch or bending rail also in the case of the support distance being changed.

In a further embodiment of the device according to the invention, a punch is provided between the counter bearings, on which the bearing blocks rest. The punch is arranged such that the position of the bearing blocks can be changed perpendicular to the base plate by using the punch. By using a punch, the positioning of the bearing blocks perpendicular to the base plate can be precisely adjusted. In this case, a punch can be provided, which comprises a base surface for support on the base plate and a surface for supporting the bearing blocks at least partially parallel thereto. Thus the positioning of the bearing blocks perpendicular to the base plate can also be adjusted by inserting or withdrawing the punch.

In a further embodiment of the punch, the punch comprises two support surfaces inclined towards a base surface and base surfaces adapted to the support surfaces are provided on the bearing blocks. The weight of the bearing blocks can exert a return force on the bearing blocks via the support surfaces inclined to the base surface and the correspondingly adapted bearing blocks, which acts at least partially perpendicular to the contact surface of the bearing blocks. Thus the bearing blocks are held via the contact surfaces on the counter bearings.

In a further embodiment of the device according to the invention, changeable inserts are provided as the means for the perpendicular change of position of the bearing blocks to the base plate, which can be arranged between the base plate and the bearing blocks. The changeable inserts preferably comprise two at least partially parallel surfaces such that a well-defined parallel offset of the bearing blocks can be effected via the inserts over the thickness of the inserts. In particular, inserts can be arranged between punch and base plate and/or between punch and bearing blocks. Depending on the angular ratios and positioning of the inserts, different changes of the distance of the counter bearings then result.

In particular, a number of inserts is available, in particular also with different dimensions, thus the change of position of the bearing blocks perpendicular to the base plate or the distance of the supports can be precisely and flexibly adjusted. The inserts are preferably formed by sheet metal layers.

In a further embodiment of the device according to the invention, a spindle is provided as the means for the perpendicular change of position of the bearing blocks to the base plate, which is arranged between the base plate and the bearing blocks, in particular between punch and base plate and/or between punch and bearing blocks. Using a spindle, which for example comprises an outer thread and is arranged in a corresponding thread in the base plate, a punch or in the bearing blocks, the position of the bearing blocks perpendicular to the base plate can be continuously adjusted. In particular, the spindle is aligned approximately perpendicular to the connection line of the supports and in particular approximately perpendicular to the base plate. Approximately perpendicular here means an angle of 90±10°. Thus only small lateral forces act on the spindle during a bending test and sufficient rigidity of the device is ensured.

According to a further embodiment of the invention, each counter bearing comprises a part connected to the base plate and at least one support plate, wherein the support plate provides the inclined contact surface to the respective bearing block. The part of the counter bearing connected to the base plate serves for deflecting the forces during the bending test into the base plate and thus ensures very high accuracy of the measurement. Unlike the variants previously described, the position of the supports can be changed only parallel to the base plate in a simple manner by exchanging the support plates. The support plates can, to this end, comprises different thicknesses, which at the same time provide different distances of the supports or bearing blocks.

If, according to a further embodiment of the device, means for the change of position of the support plates perpendicular to the base plate are provided, the position of the supports and thus of the bearing blocks can be changed only in the horizontal direction via the inclined contact surface of the support plate without the height of the supports being changed. The support plates, to this end, preferably comprise a wedge-shaped cross-sectional area.

According to a further embodiment, at least one spindle, at least one insert and/or at least one punch can be provided as the means for the change of position of the support plates perpendicular to the base plate. Spindles, punches and inserts can be used for the direct change of position of the support plates perpendicular to the base plate. A simultaneous change of position of the bearing blocks perpendicular and parallel to the base plate is also possible when using punches, spindles and inserts.

The device according to the invention can be further improved by providing at least one horizontally displaceable wedge element as the means for changing the position of the support plates perpendicular to the base pate, said wedge element is engaged with a sliding element comprising an inclined contact surface to the wedge element such that the position of the sliding element can be changed perpendicular to the base plate by displacing the at least one wedge element, wherein the at least one sliding element is engaged with the support plates in such a way that the position of the support plates perpendicular to the base plate is changeable when the position of the sliding element is changed. Via the wedge element and the sliding element, very precise changing of the position of the support plates can be utilised by way of a reduction ratio with regard to the position displacement of the wedge element and the transfer of the movement thereof to a change of position of the sliding element perpendicular to the base plate. The highly precise change of position of the support plates perpendicular to the base plate leads directly to the highly precise displacement of the bearing blocks parallel to the base plates via the inclined contact surfaces.

A particularly simple and at the same time very precise possibility to displace the at least one wedge element, is achieved according to a further embodiment by providing a spindle for the horizontal displacement of the wedge element. A reduction transmission ratio with regard to a rotation of the spindle in relation to the movement of the wedge element can be selected via the spindle such that the displacement of the bearing blocks takes place very precisely. Since the support plates deflect only a small part of the occurring bending forces on the sliding element owing to the inclined contact surfaces, high forces are also not transferred on the spindle during the bending test. By using a spindle and a reduction transmission ratio, the position of the spindle and thus the distance of the bearing blocks to each other can be set in a simple manner, securely locked in a fixed relation. Advantageously, this embodiment can thus be further improved by providing a reading device on the spindle in order to be able to read the distance of the supports directly on the spindle.

The previous embodiments can thus be further improved by providing step motors which carry out the positioning of the bearing blocks exactly and reproducibly, for example via driven spindles. The spindle can for example be driven via step motors. There is in particular the possibility of performing the bending test in an automated manner.

In a further embodiment of the device according to the invention, a tensioning element, in particular a spring element is provided between the bearing blocks. Such a tensioning element, for example a spring element or an element made from an elastic material, exerts a return force on the bearing blocks which acts at least partially perpendicular to the contact surface of the bearing blocks. The bearing blocks are thus held on the counter bearings via the contact surfaces.

In a further embodiment of the device according to the invention, connection means are provided which connect the counter bearings at least partially in the direction to the connection line of the supports and/or connect the counter bearings at least partially in the direction to the connection line of the supports with the base plate. The stability and rigidity or bending stiffness of the arrangement of counter bearings and base plate can be further improved by way of such connection means, which increase the measurement accuracy, in particular in the case of high forces during the bending test. The counter bearings can thus for example be mutually supported via struts or plates. Similarly, the connection of counter bearings and base plate can be further supported by connection means, for example in the form of crossed struts or a plate which is fastened to counter bearings and to the base plate. A connection of the connection means to the counter bearings and to the base plate can, in particular be effected in a positive manner via pinning or screwing, but also in a materially-bonded manner via adhesive, welding or brazing or a combination thereof.

In a further embodiment of the device according to the invention, openings are provided in the connection means for observing the bending sample and/or changing the punch or the inserts. By way of openings in the corresponding regions, the stability of the arrangement of counter bearings and base plate can be increased, as already stated, through the connection means without the user-friendliness of the arrangement being impacted.

In a further embodiment of the device according to the invention, the counter bearings are connected to the base plate in a materially-bonded manner. Since the device according to the invention does not require the counter bearings to be adjusted, a materially-bonded connection can further improve the stability of the arrangement of base plate and counter bearings. In particular, counter bearings and base plate can constitute a single component, i.e. made from one piece. Counter bearings and base plate can, however, also be manufactured as separate components and be subsequently connected by a materially-bonded connection method, for example welding, adhering or brazing.

In a further embodiment of the device according to the invention, cylinder segment-shaped surfaces, in particular rollers are provided as the supports. Cylinder segment-shaped surfaces have the advantage of providing a uniform, in particular straight support surface for the bending sample during the bending test in spite of a changing bending angle. The supports can also have a completely cylindrical shape and in particular be rotatably mounted as rollers.

In a further embodiment of the device according to the invention, the bending punch or bending rail is configured for a 3 point bending test, in particular for a platelet bending test or a 4 point bending test. The device according to the invention is in particular suitable for the high loads occurring under certain circumstances in the case of 3 point or 4 point bending tests. The bending punch or the bending rail can also have an exchangeable profile such that a contact surface of the bending punch or bending rail can be switched between 3 point and 4 point bending tests or a worn contact surface of the bending punch or bending rail can also be replaced.

According to a second technical teaching of the present invention, the above-mentioned technical problem concerning a method using a device according to the invention is solved in which a bending sample is applied on the supports and in which a force is exerted between the supports on the bending sample.

As already mentioned regarding the device according to the invention, this is particularly suitable for receiving high forces without the distance of the supports that is critical for the measurement result notably changing. Consequently, bending tests can be performed using the device according to the invention, in which the forces exerted are large and in particular high bending angles can be obtained. In the case of high bending angles, high forces result parallel to the connection line of the supports, which can be received in a convenient manner by the inclined contact surfaces of counter bearings and bearing blocks. High measurement accuracy in the bending test can thus be obtained using the device according to the invention owing to a substantially constant distance of the supports.

The force of the bending punch or bending rail and a bending angle of the bending sample produced by the force are in particular measured in the method according to the invention. The force-path characteristic curve of the material of the bending sample is thus recorded.

Different sample geometries of the bending sample are conceivable in the method according to the invention. In a preferred embodiment, the bending sample has a platelet shape, strip shape or sheet metal shape. The bending sample can thus be applied with one surface on the supports and the measurement geometry for a 3 point or 4 point bending test is well-defined, i.e. the support points or starting points for the bending force are easily specified.

According to a further embodiment of the method according to the invention, the distance of the supports is set via means for changing the position of the bearing blocks prior to applying the bending sample. In particular, the distance of the supports can thus be adapted to the sample geometry. A series of measurements can also be performed on a determined sample geometry using different distances. Using the device according to the invention, the distance of the supports can in particular be set without negatively affecting the stability of the device with regard to high bending forces such that particularly accurate measurement results can be obtained.

BRIEF DESCRIPTION OF THE SEVERAL VIEWS OF THE DRAWING

With regard to further embodiments and advantages of the method, reference is made to the above descriptions regarding the device according to the invention as well as to the drawings. They show.

DETAILED DESCRIPTION OF THE INVENTION

Figure 1:
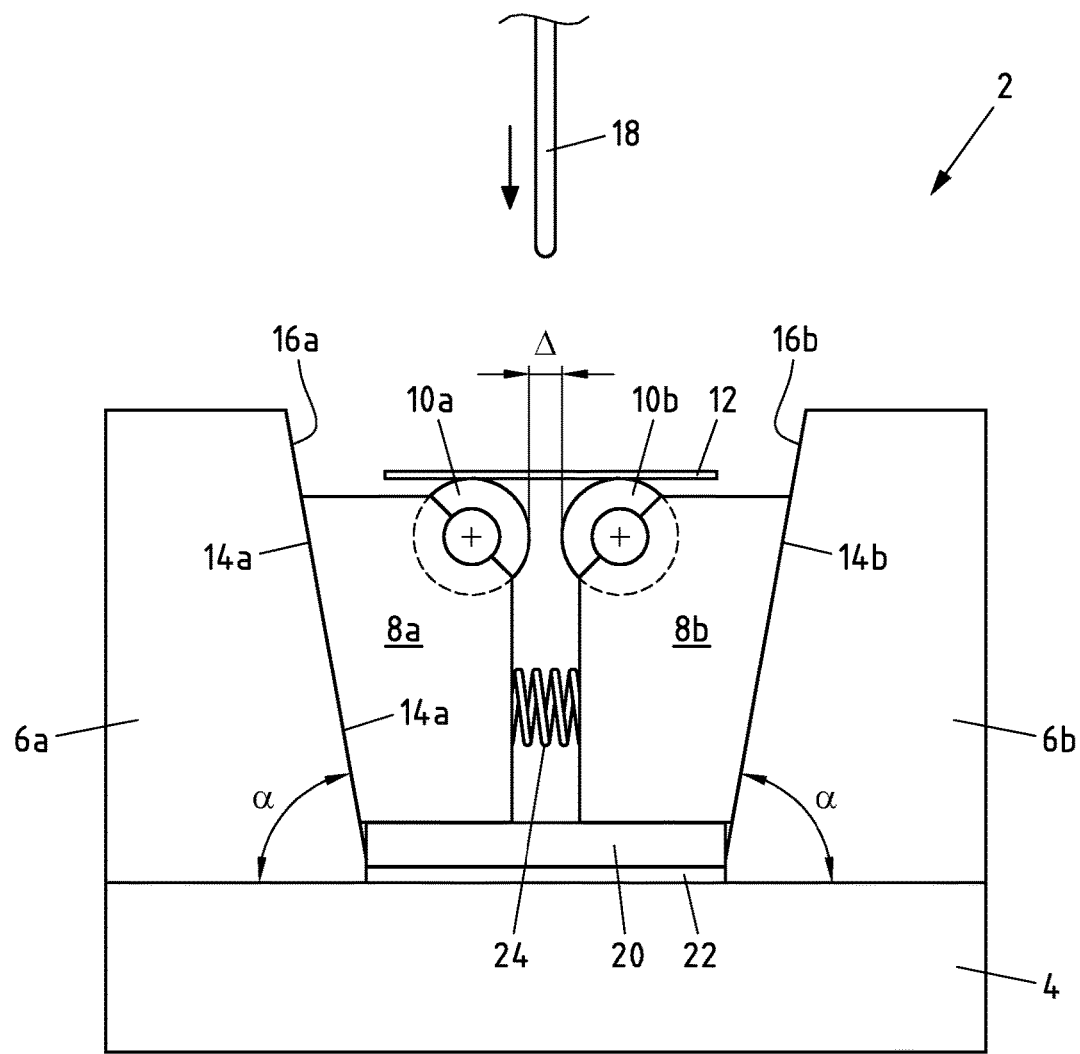
FIG. 1 shows a first exemplary embodiment of the device according to the invention in a schematic view.

FIG. 1 shows a first exemplary embodiment of the device 2 according to the invention in a schematic view. Counter bearings 6a, 6b are connected to each other via a base plate 4. The connection between base plate 4 and counter bearings 6a, 6b can, for example take place by way of pinning, preferably however the connection is materially-bonded. The arrangement of the base plate 4 with the counter bearings 6a, 6b is very rigidly designed and does not have to be adjustable, i.e. the counter bearings 6a, 6b can be arranged undetectably on the base plate 4.

Bearing blocks 8a, 8b are arranged in the space between the counter bearings 6a, 6b. The bearing blocks 8a, 8b are, in this arrangement, in particular separate components and exchangeable or displaceable relative to the base plate 4 and counter bearings 6a, 6b.

Supports 10a, 10b are arranged on the bearing blocks 6a, 6b, said supports 10a, 10b having a cylinder segment-shaped outer contour, in particular in the shape of rotatably mounted rollers. The supports 10a, 10b form in particular two contact lines or contact points, on which a bending sample 12 is applied, which in particular has a platelet, strip or sheet metal shape.

The bearing blocks 8a, 8b abut on correspondingly inclined contact surfaces 16a, 16b of the counter bearings 6a, 6b via contact surfaces 14a, 14b inclined relative to the base plate 4. The angle of the contact surfaces 14a, 14b; 16a, 16b is designated with $\alpha$ in FIG. 1.

The device 2 in relation to a mirror plane is in particular symmetrical. For this purpose, the counter bearings 6a, 6b and the bearing blocks 8a, 8b can in each case have the same geometry and the same inclination angle $\alpha$. The mirror plane then runs between the counter bearings 10a, 10b.

In order to exert a force on the bending sample 12, a bending punch or bending rail 18 is provided. It is arranged such that a force can be exerted on the bending sample 12 between supports 10a, 10b and the bending sample 12 can be deformed with a bending angle.

In this exemplary embodiment, the bending punch or bending rail 18 is configured for a 3 point bending test. A bending punch or bending rail 18 can also be provided with two contact points for a 4 point bending test.

The distance $\Delta$ between the supports 10a, 10b can in principle be set via differently dimensioned bearing blocks 8a, 8b. In order to set the distance $\Delta$ between the supports 10a, 10b, means for changing the position of the bearing blocks 8a, 8b perpendicular to the base plate 4 can also, however, be used. In this exemplary embodiment, a punch 20 is arranged between the counter bearings 6a, 6b on the base plate 4. The punch 20 is, in particular, a separate component and can be removed or exchanged for another punch 20 with a different height. Via a change of position of the bearing blocks 8a, 8b perpendicular to the base plate 4 by the punch 2, the position of the bearing blocks 8a, 8b parallel to the base plate 4 and thus the distance $\Delta$ between the supports 10a, 10b is also changed via the inclined contact surfaces 14a, 14b; 16a, 16b. The distance $\Delta$ can thus be set by a determined height of the punch 20 depending on the angle $\alpha$.

The angle $\alpha$ is preferably between 70° and 90°, in particular between 75° and 85°. An angle $\alpha$ of 80.54°, for example gives a transmission of about 4:1 between the positioning of the bearing blocks 8a, 8b perpendicular and parallel to the base plate 4. A punch 20 with a height of 4 mm then gives for example an increase of the distance $\Delta$ by 1 mm.

Moreover, inserts 22 can be provided, which can be inserted between the base plate 4 and the bearing blocks 6a, 6b for the change of position of the bearing blocks 6a, 6b perpendicular to the base plate 4. The inserts 22 can be arranged between punch 20 and base plate 4, as shown in FIG. 1 and/or between punch 20 and bearing blocks 8a, 8b. In particular, a number of inserts 22 are available, in particular also with different dimensions, thus the change of position of the bearing blocks 6a, 6b perpendicular to the base plate 4 or the distance $\Delta$ of the supports 10a, 10b can be set precisely and flexibly. In particular, the inserts 22 comprise at least partially parallel surfaces. The inserts 22 are preferably formed by sheet metal-shaped layers.

The device 2 can also comprise a pretensioning element, for example in the form of a spring element 24 between the bearing blocks. As a result, pretension is exerted on the bearing blocks 8a, 8b which presses the bearing blocks 8a, 8b with the contact surfaces 14a, 14b; 16a, 16b against the counter bearing 6a, 6b. The setting of the distance Δ of the supports 10a, 10b is thus particularly accurate since a play between bearing blocks 8a, 8b and the counter bearings 6a, 6b is avoided.

Figure 2:
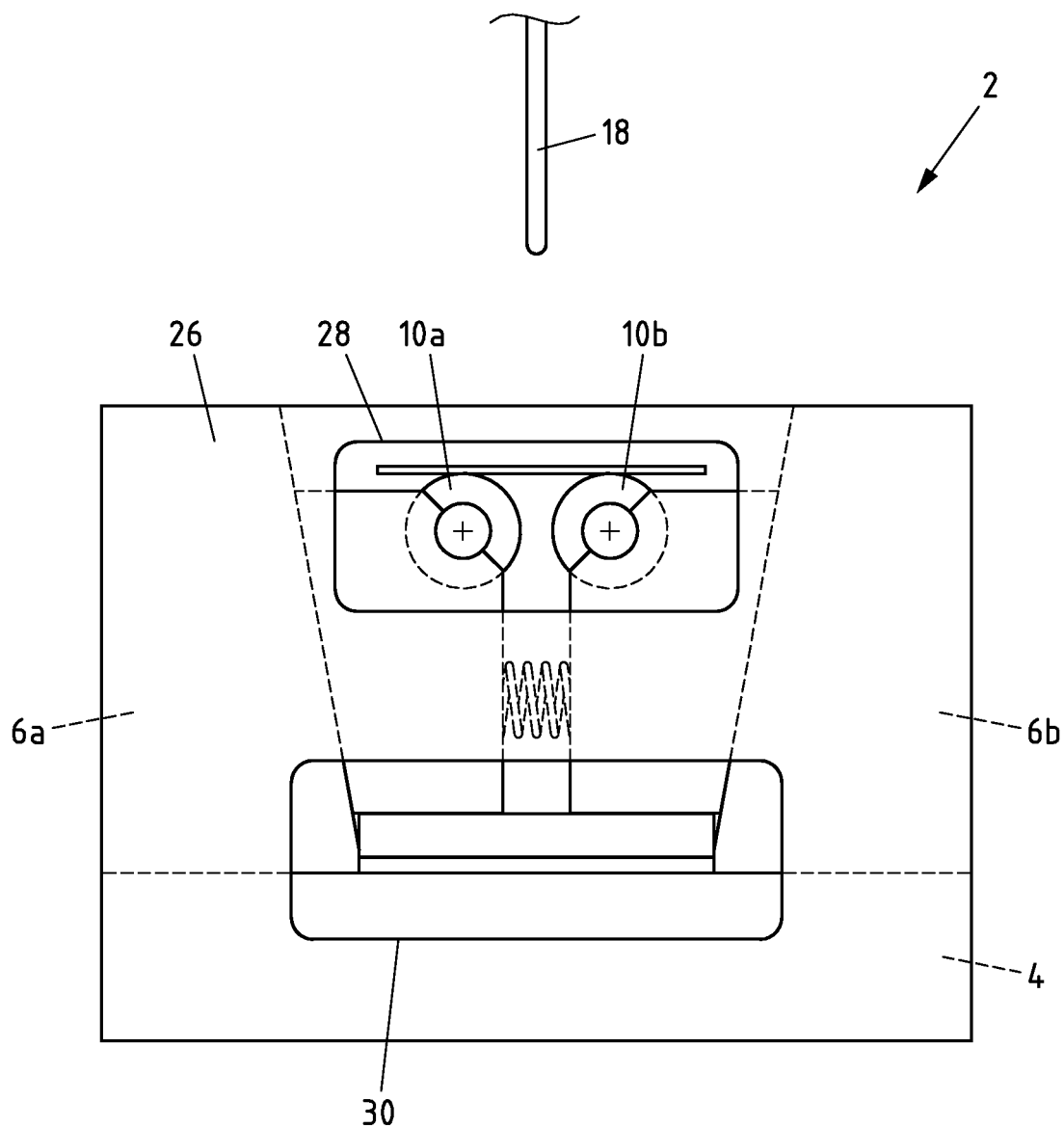
FIG. 2 shows a second exemplary embodiment of the device according to the invention in a schematic side view.

FIG. 2 shows a second exemplary embodiment of the device 2 according to the invention in a schematic side view. Here the structure of the device 2 is identical to the structure of the exemplary embodiment shown in FIG. 1, wherein in FIG. 2 some reference numerals have been omitted for the sake of clarity. The device 2 shown in FIG. 2 comprises connection means in the form of a connection plate 26, which connects the counter bearings 6a, 6b at least partially in the direction to the connection line of the supports 10a, 10b and connects the counter bearings 6a, 6b at least partially in the direction to the connection line of the supports 10a, 10b to the base plate 4. The connection plate 26 is, in this arrangement, located at the side of the bearing blocks 8a, 8b such that the device 2 is open at the top to use the bending punch or bending rail 18. In particular, a further connection plate (not shown) can be arranged on the other side. Such connection means 26 can further improve the stability and rigidity or bending stiffness of the arrangement of counter bearings 6a, 6b and base plate 4, which increases the measurement accuracy in particular in the case of high forces during the bending test.

For example, the connection means 26 can comprise openings 28, 30. The opening 28 can serve for observing the bending sample and the opening 30 can be provided for changing the inserts 22 or the punch 20.

Figure 3:
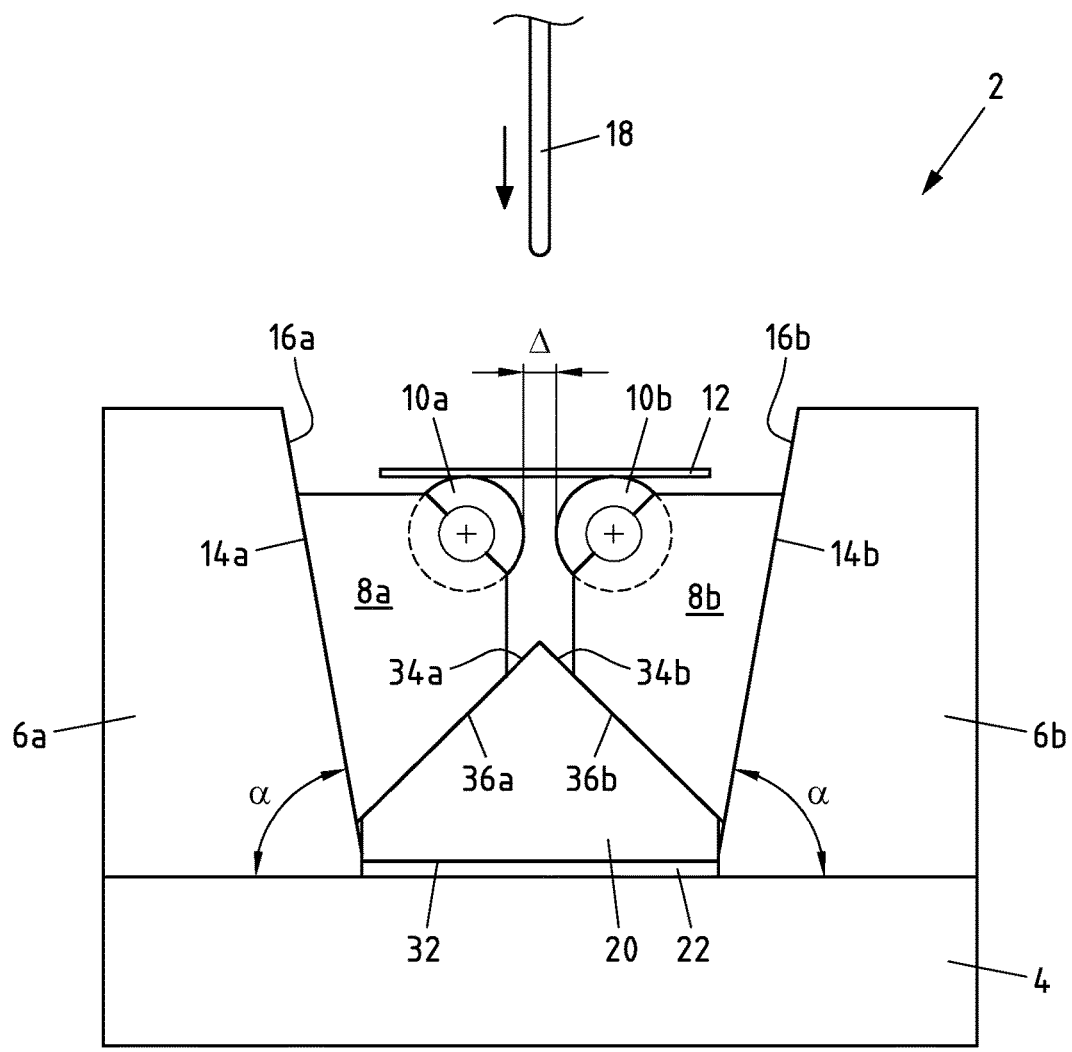
FIG. 3 shows a third exemplary embodiment of the device according to the invention in a schematic view.

FIG. 3 shows a third exemplary embodiment of the device 2 according to the invention in a schematic view. A punch 20 is provided here, which comprises two support surfaces 34a, 34b inclined towards a base surface 32 and base surfaces 36a, 36b adapted to the support surfaces 34a, 34b are provided on the bearing blocks 8a, 8b. By way of the inclined support surfaces 34a, 34b and base surfaces 36a, 36b, the bearing blocks 8a, 8b are pressed against the contact surfaces 16a, 16b owing to their weight and are thus pretensioned. The distance Δ between the supports 10a, 10b can thus be set particularly precisely.

Setting the distance Δ can in turn be effected via a change of position of the bearing blocks 8a, 8b, in particular by using inserts 22. The inserts 22 can be arranged between punch 20 and base plate 4, as shown in FIG. 3, and/or between punch 20 and bearing blocks 8a, 8b.

Figure 4:
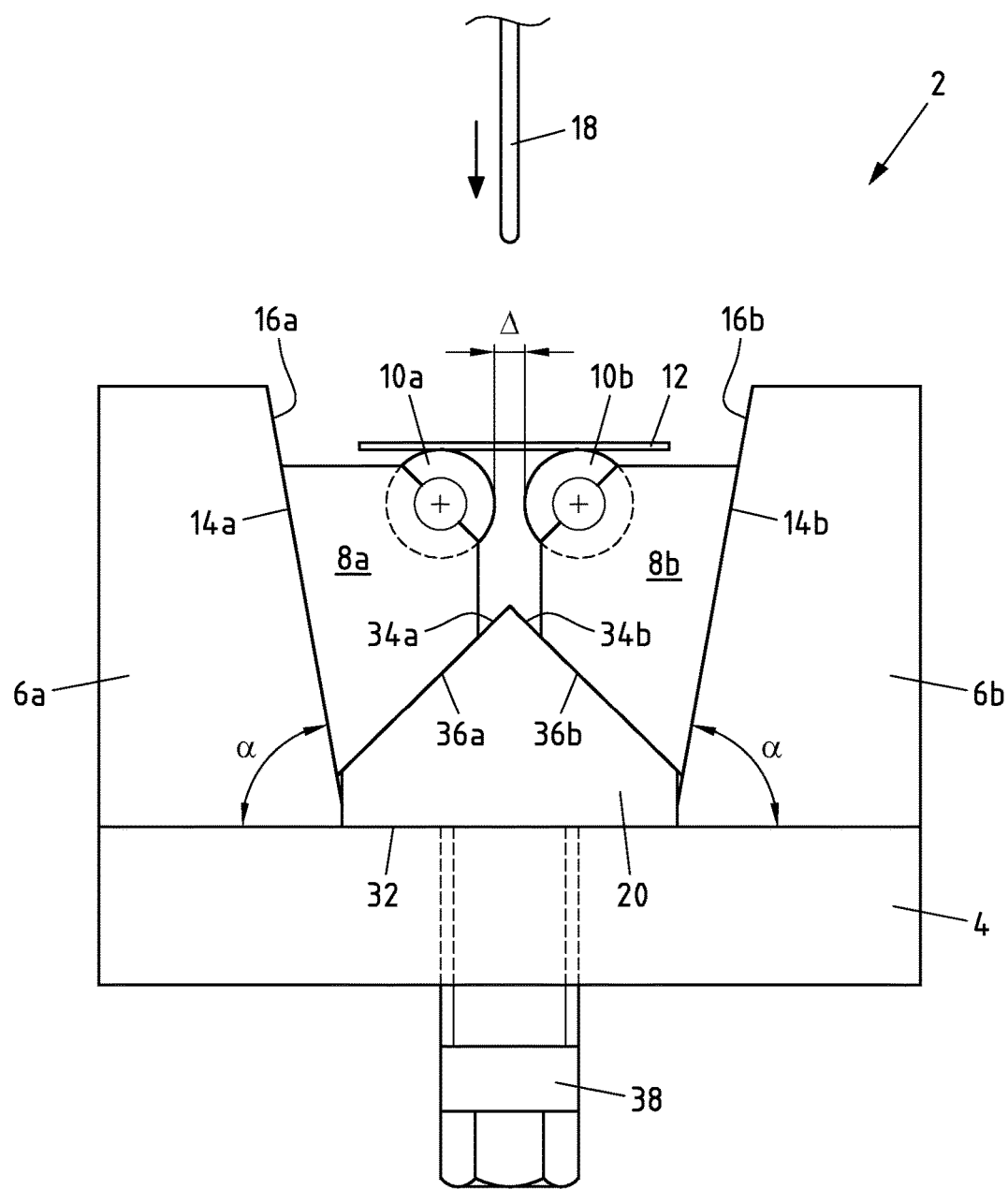
FIG. 4 shows a fourth exemplary embodiment of the device according to the invention in a schematic view.

FIG. 4 shows a fourth exemplary embodiment of the device 2 according to the invention in a schematic view, wherein a spindle 38 is provided as the means for the change of position, which is arranged between punch 20 and base plate 4. Setting the distance Δ via a change of position of the bearing blocks 8a, 8b is also possible via the spindle 38. The position of the bearing blocks 8a, 8b perpendicular to the base plate 4 can be set continuously using the spindle 38. The spindle 38 is arranged approximately perpendicular to the base plate. Only small lateral forces thus act on the spindle 38 during a bending test.

Figure 5:
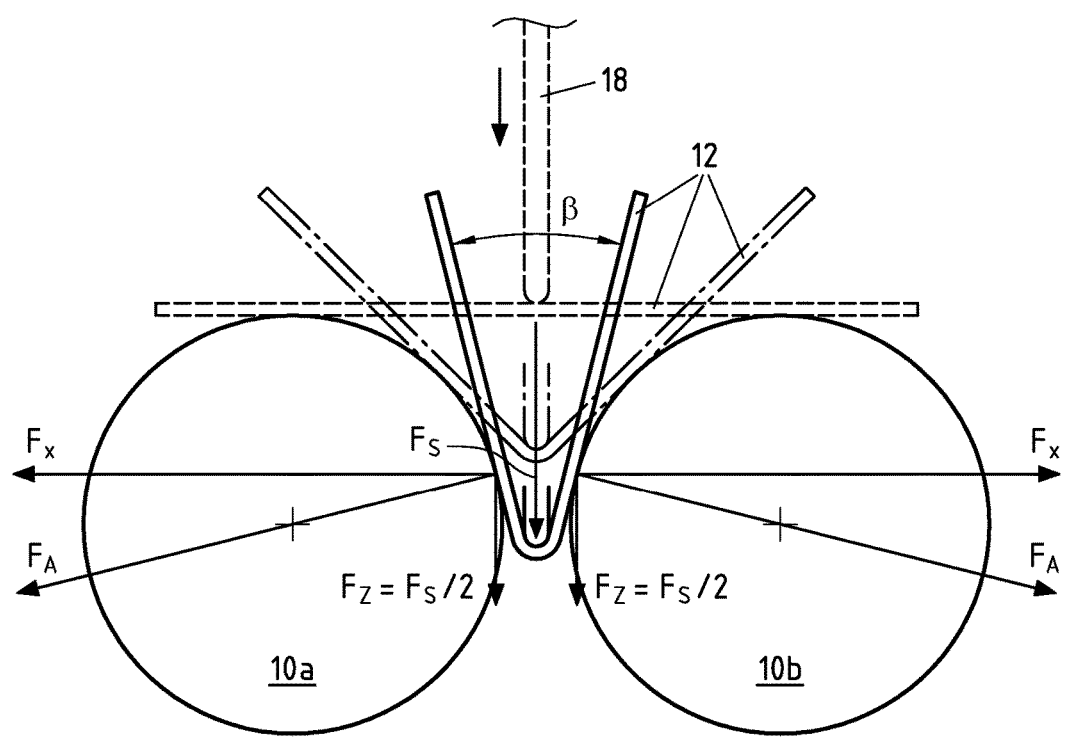
FIG. 5 shows a schematic detail view of the supports during a bending test.

FIG. 5 lastly shows a schematic detail view of the supports 10a, 10b during a bending test for clarifying the force ratios. A bending sample 12, which is shown here as a platelet, is firstly applied on the supports 10a, 10b. The bending punch or the bending rail 18 is then lowered until it contacts the surfaces of the bending sample 12. A force $F_S$ is then exerted via the bending punch or the bending rail 18 in the direction of the arrow on the bending sample 12 between the supports 10a, 10b and the bending sample 12 is deformed at an opening angle β. A continuous deformation is indicated in FIG. 4 via the dashed, dot-dashed and solid lines for bending sample 12 and bending punch or bending rail 18. A continuous measurement of the opening angle β for example takes place, in particular regarding the position of the bending punch or the bending rail 18 and the force $F_S$ of the bending punch or the bending rail 18.

The force $F_A$ acting on the supports 10a, 10b is also illustrated for the illustration of the solid lines for bending sample 12 and bending punch or bending rail 18. This force results through the persistence of the bending sample 12 against the deformation by the force of the bending punch or the bending rail $F_S$. What was problematic for existing measuring devices was that the component $F_X$ acting in the direction of the connection line of the supports with decreasing opening angle β, i.e. increasing bending angle, can be very large. $F_X$ is calculated by $$F_X = 0.5 * F_S * \cot(\beta/2).$$

$F_X$ thus strives for small angles β, even towards infinite. The supports 10a, 10b must thus be capable of receiving correspondingly large forces without the distance Δ that is critical for the measurement notably changing.

This is achieved via the device according to the invention or the method according to the invention. In particular via the inclined contact surfaces 14a, 14b; 16a, 16b, the force $F_A$ can be advantageously received without large leverage effects via the bearing blocks 8a, 8b being produced.

Figure 6:
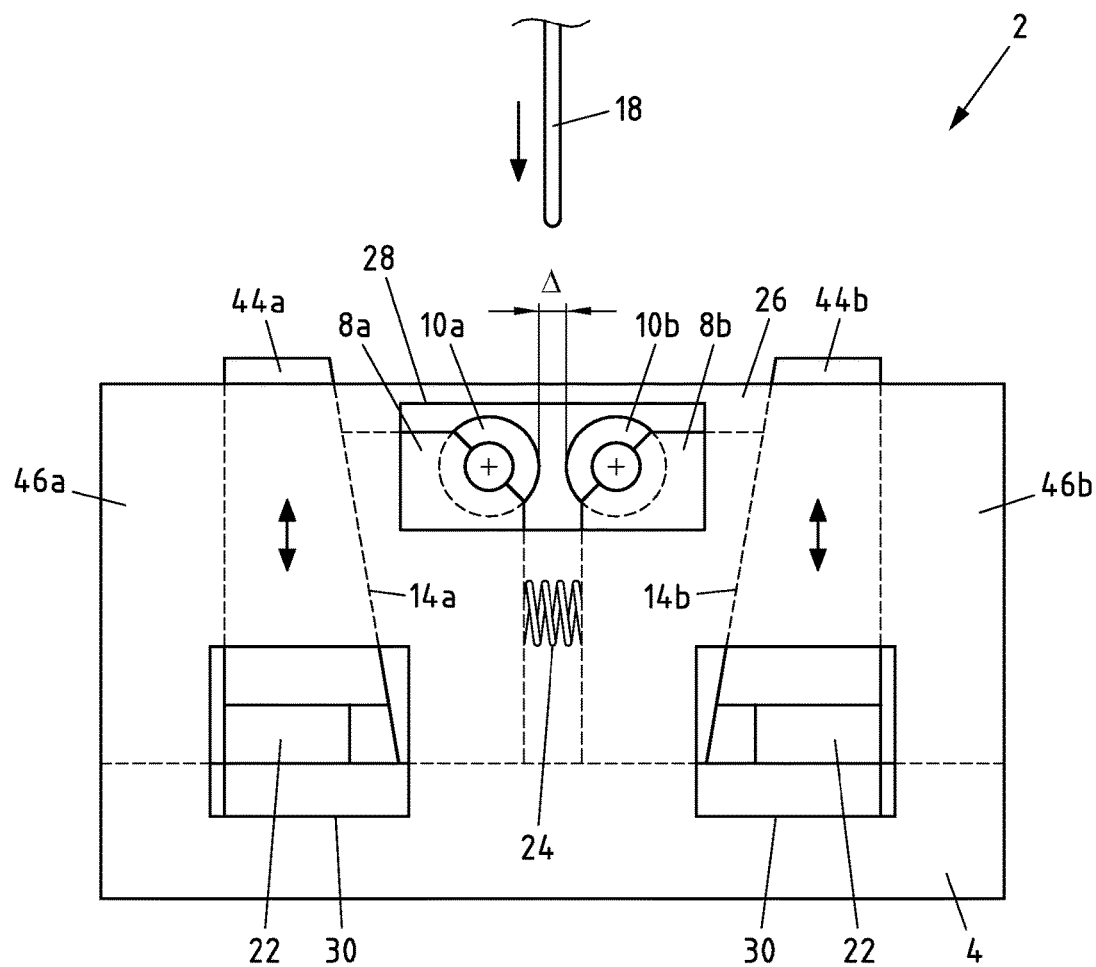
FIGS. 6 to 9 show four further exemplary embodiments of the device according to the invention in a schematic view.

FIG. 6 shows an exemplary embodiment of the device according to the invention with means for the change of position of the bearing blocks 8a, 8b parallel to the base plate in a schematic view. The counter bearings in the exemplary embodiment illustrated in FIG. 6 in each case comprise a part 46a, 46b connected to the base plate as well as a support plate 44a, 44b. The support plates 44a, 44b in each case comprise inclined contact surface 48a, 48b to the respective bearing block 8a, 8b. The distance of the bearing blocks 8a, 8b can be changed by exchanging the support plates 44a, 44b comprising a wedge-shaped cross-sectional area. In addition, the position of the support plates 44a, 44b can be changed perpendicular to the base plate 4 by the inserts 22 such that the distance of the bearing blocks 8a, 8b can also be changed by exchanging the inserts 22.

Figure 7:
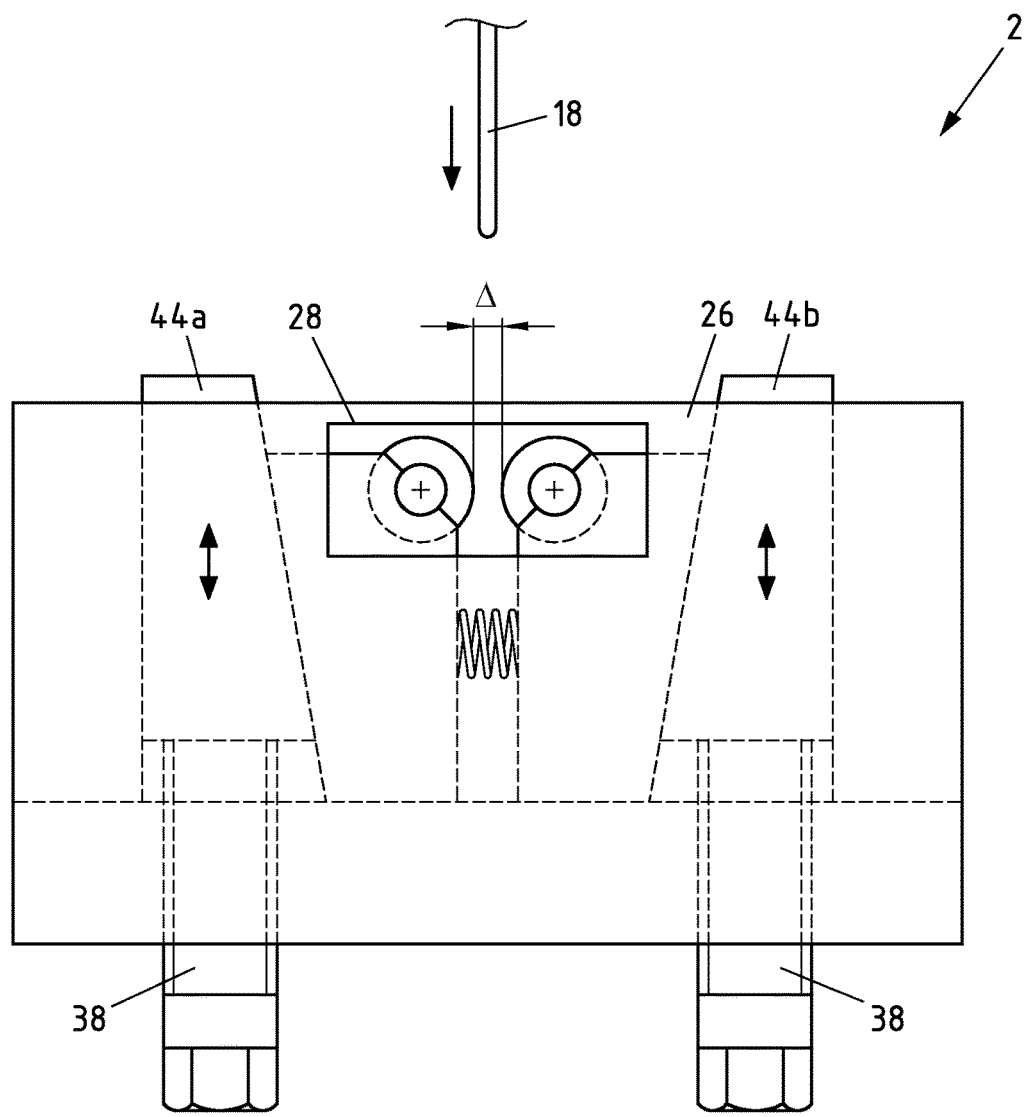

FIG. 7 shows a further exemplary embodiment of the device according to the invention in a schematic view, in the case of which spindles 38 are provided instead of the inserts 22, said spindles can change the position of the support plates 44a, 44b perpendicular to the base plate 4. Only a small part of the bending forces is transferred to the spindles 38 by the inclined contact surfaces of the support plate to the bearing block such that the spindles 38 can maintain precisely the position of the support plates 44a, 44b during the bending test, for example by using a locking mechanism of the spindle that is not illustrated.

Figure 8:
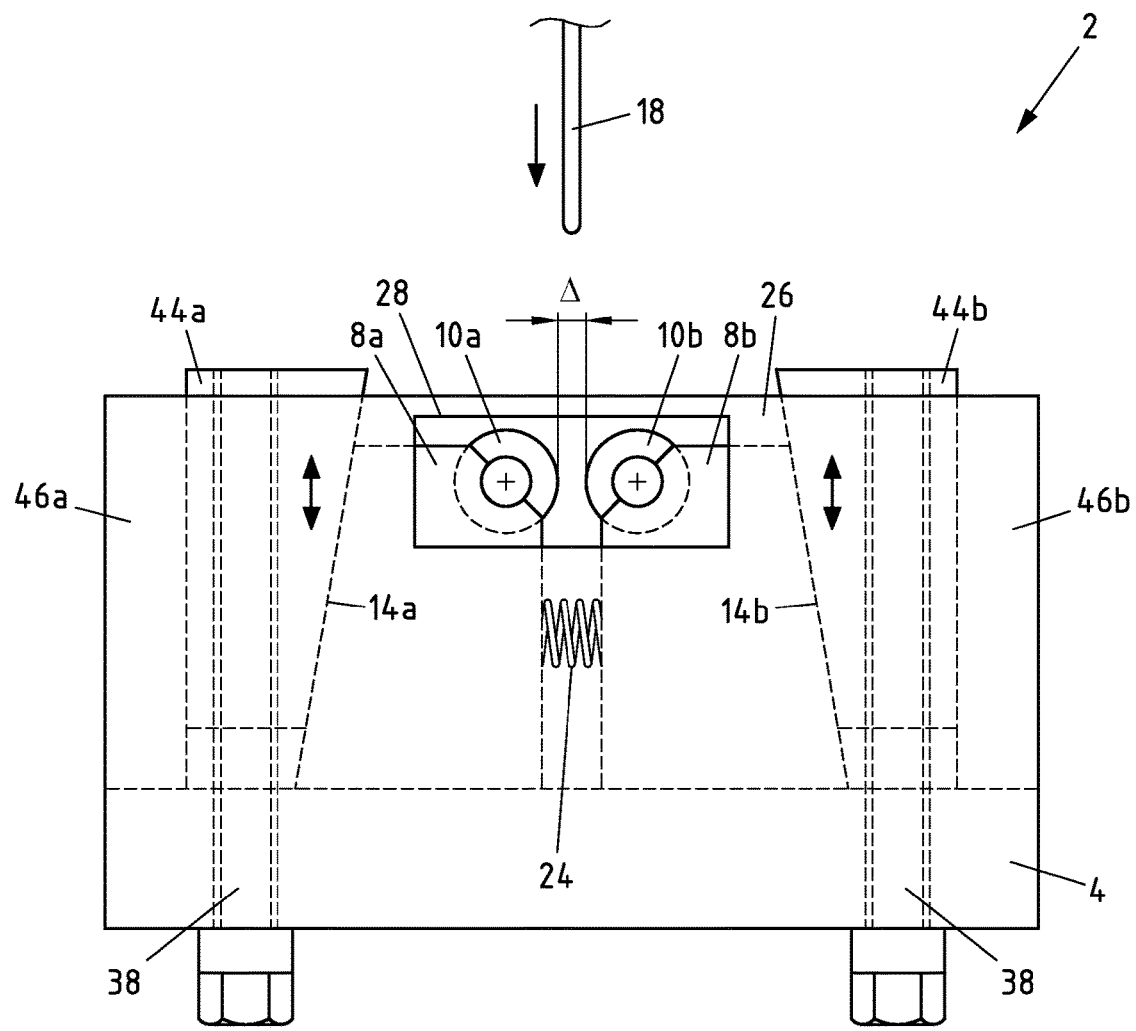

The inclined contact surfaces between the bearing blocks 8a, 8b and the counter bearings or the support plates 44a, 44b can run such that in the direction of the bending punch the support plates 44a, 44b occupy a larger distance to each other or vice versa that the support plates 44a, 44b have a smaller distance to each other in the direction of the bending punch. FIG. 8 shows an exemplary embodiment, in the case of which, unlike the exemplary embodiment in FIG. 7, the inclined contact surfaces 14a, 14b in the direction of the bending punch 18 lead to a reduced distance of the support plates 44a, 44b to each other. The spindles 38 are subjected to tensile stress during the bending test by way of the inclined contact surfaces 14a, 14b between the bearing blocks 8a, 8b illustrated in FIG. 8, unlike in the exemplary embodiment in FIG. 7. A locking of the spindles 38 is also possible here, for example via a force lock means.

Figure 9:
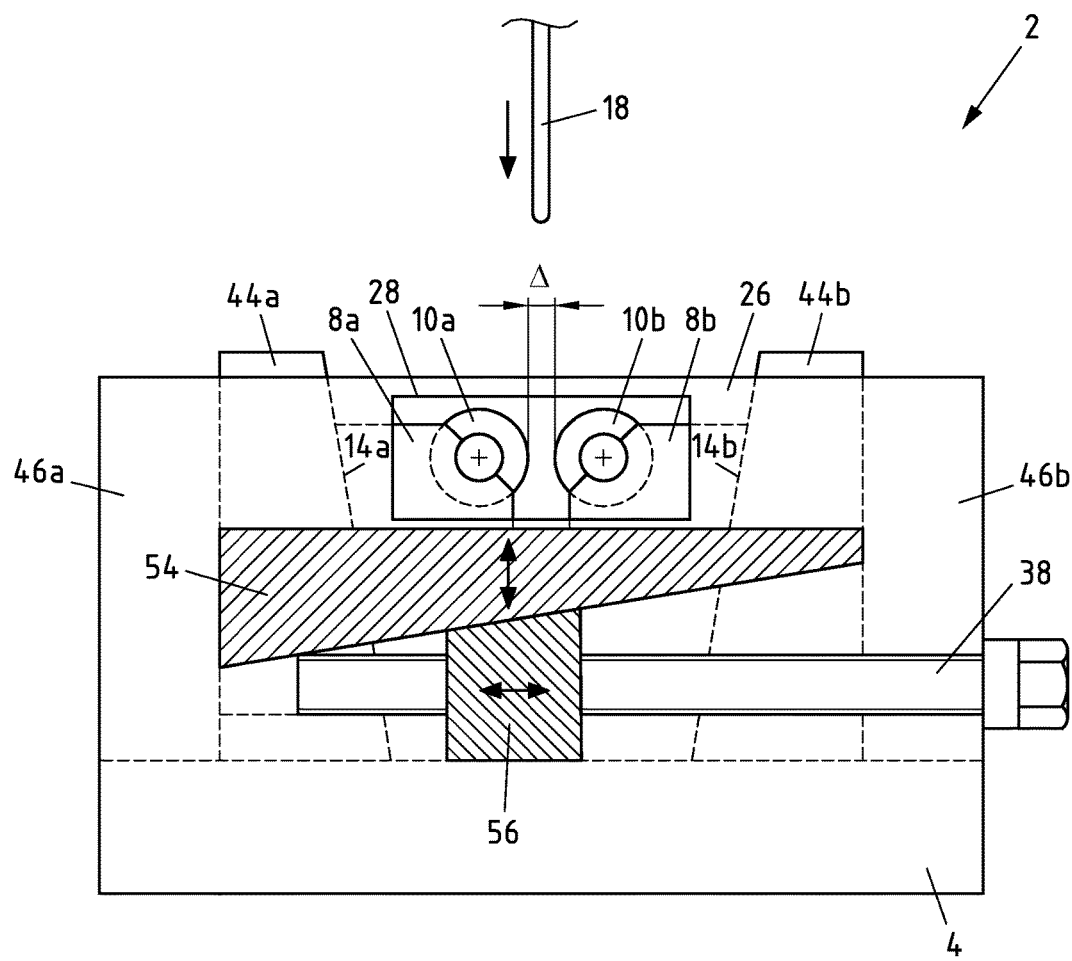

FIG. 9 lastly shows a subsequent exemplary embodiment, in the case of which at least one horizontally displaceable wedge element 56 is provided as the means for the change of position of the support plates perpendicular to the base plate, said wedge element is engaged with a sliding element 54 comprising an inclined contact surface to the wedge element 56 such that the position of the sliding element 54 can be changed perpendicular to the base plate 4 by displacing the at least one wedge element 56, wherein the at least one sliding element 54 is engaged with the support plates 44a, 44b in such a way that the position of the support plates 44a, 44b perpendicular to the base plate is changeable when the position of the sliding element 54 is changed. The movement of the wedge element 56 takes place in the present exemplary embodiment via a spindle 38, which leads to a change of position of the at least one sliding element 54 perpendicular to the base plate via the engaged and inclined contact surfaces of the wedge element 56 and of the sliding element 54. By way of the inclined contact surfaces and the forced guidance of the sliding element 54 by means of the wedge element, there is not only being givena particularly simple possibility of changing the position of the support plates 44a, 44b using the at least one sliding element 54. Owing to the inclined contact surfaces of wedge element 56 and sliding element 54, there is also the possibility of achieving a very precise height adjustment, for example in the micrometre range, of the sliding element 54 due to the reduction of the horizontal movement of the wedge element 56 into a vertical movement of the sliding element 54.

The spindle 38 can, not illustrated here, comprise a display which shows the distance of the supports 10a, 10b and thus directly gives the user information on the support distance that has been set. The position of the bearing blocks and thus of the supports 10a, 10b can be very precisely set by using the inclined contact surfaces between wedge element 56 and sliding element 54 as well as via the increase of the thread of the spindle 38.

In all three illustrated exemplary embodiments of FIGS. 6 to 9, the parts 46a, 46b of the counter bearing connected to the base plate are, for example connected to the base plate via a positive connection and/or force fit connection or also in a materially-bonded manner. Pinning of the counter bearing parts 46a, 46b is for example possible for a positive connection. A force fit connection can, for example take place via screwing to a force fit and positive connection with the base plate 4. A materially-bonded connection or also an integral formation of the base plate with counter bearing parts 46a, 46b is, however, also conceivable. The same also applies of course for the connection of the counter bearings 6a and 6b of FIGS. 1 to 4.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A device for performing a bending test
having a base plate,
having counter bearings connected via the base plate,
having bearing blocks, which in each case comprise a support for applying a bending sample to, and
having a bending punch or a bending rail for exerting a force on the bending sample,
characterised in that
the counter bearings and the bearing blocks abut against each other via contact surfaces inclined to the base plate.

2. The device according to claim 1,
characterised in that
means for changing the position of the bearing blocks perpendicular and/or parallel to the base plate are provided, wherein a change of the distance of the supports can be effected with the change of position via the inclined contact surfaces.

3. The device according to claim 2,
characterised in that
changeable inserts are provided as the means for the perpendicular change of position of the bearing blocks to the base plate, which can be arranged between the base plate and the bearing blocks.

4. The device according to claim 2,
characterised in that
a spindle is provided as the means for the perpendicular change of position of the bearing blocks to the base plate, which is arranged between the base plate and the bearing blocks.

5. The device according to claim 2,
characterised in that
changeable inserts are provided as the means for the perpendicular change of position of the bearing blocks to the base plate, which can be arranged between the punch and base plate and/or between punch and bearing blocks.

6. The device according to claim 2,
characterised in that
a spindle is provided as the means for the perpendicular change of position of the bearing blocks to the base plate, which is arranged between punch and base plate and/or between punch and bearing blocks.

7. The device according to claim 1,
characterised in that
a punch is provided between the counter bearings, on which the bearing blocks rest such that the position of the bearing blocks can be changed perpendicular to the base plate via the punch.

8. The device according to claim 7,
characterised in that
the punch comprises two support surfaces inclined towards a base surface and
base surfaces adapted to the support surfaces are provided on the bearing blocks.

9. The device according to claim 1,
characterised in that
each counter bearing in each case comprises a part connected to the base plate and at least one support plate, wherein the support plate provides the inclined contact surface to the respective bearing block.

10. The device according to claim 9,
characterised in that
means are provided for the change of position of the support plates perpendicular to the base plate.

11. The device according to claim 10,
characterised in that
openings are provided in the connection means for observing the bending sample and/or for changing the punch or the inserts.

12. The device according to claim 1,
characterised in that
spindles, inserts and/or punches are provided as the means for the change of position of the support plates perpendicular to the base plate.

13. The device according to claim 1,
characterised in that
at least one horizontally displaceable wedge element is provided as the means for the change of position of the support plates perpendicular to the base plate, said wedge element is engaged with a sliding element comprising an inclined contact surface to the wedge element such that the position of the sliding element can be changed perpendicular to the base plate by displacing the at least one wedge element, wherein the at least one sliding element is engaged with the support plates in such a way that the position of the support plates perpendicular to the base plate is changeable when the position of the sliding element is changed.

14. The device according to claim 1,
characterised in that
a spindle is provided for horizontally displacing the wedge element.

15. The device according to claim 1,
characterised in that
a pretensioning element is provided between the bearing blocks.

16. The device according to claim 1,
characterised in that
connection means are provided which connect the counter bearings at least partially in the direction to the connection line of the supports and/or
connect the counter bearings at least partially in the direction to the connection line of the supports to the base plate.

17. A method for performing a bending test using a device according to claim 1,
in which a bending sample is applied on the supports,
in which a force ($F_S$) is exerted between the supports on the bending sample and
optionally the forces of the bending punch or of the bending rail ($F_S$) and a bending angle of the bending sample produced by the force are measured.

18. The device according to claim 1,
characterised in that
a spring element is provided between the bearing blocks.

* * * * *